(12) United States Patent
Kitching et al.

(10) Patent No.: US 9,017,072 B2
(45) Date of Patent: *Apr. 28, 2015

(54) TREATMENT PROGRESS TRACKING AND RECALIBRATION

(71) Applicant: Align Technology, Inc., San Jose, CA (US)

(72) Inventors: Ian Kitching, Saratoga, CA (US); Rene Sterental, Palo Alto, CA (US); Eric Kuo, Foster City, CA (US); Maia Singer, Campbell, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/341,645

(22) Filed: Jul. 25, 2014

(65) Prior Publication Data

US 2014/0335466 A1 Nov. 13, 2014

Related U.S. Application Data

(63) Continuation of application No. 14/034,373, filed on Sep. 23, 2013, now Pat. No. 8,899,978, which is a continuation of application No. 11/760,705, filed on Jun. 8, 2007, now Pat. No. 8,562,338.

(51) Int. Cl.
*A61C 3/00* (2006.01)
*A61C 7/00* (2006.01)
*A61C 7/08* (2006.01)

(52) U.S. Cl.
CPC . *A61C 7/002* (2013.01); *A61C 7/00* (2013.01); *A61C 7/08* (2013.01)

(58) Field of Classification Search
USPC .......... 433/24, 215; 700/98; 705/3; 382/128, 382/181–231
See application file for complete search history.

(56) References Cited

U.S. PATENT DOCUMENTS

| | | | |
|---|---|---|---|
| 6,315,553 B1 * | 11/2001 | Sachdeva et al. | 433/24 |
| 7,357,636 B2 * | 4/2008 | Hedge et al. | 433/53 |
| 2005/0048432 A1 * | 3/2005 | Choi et al. | 433/24 |
| 2006/0079981 A1 * | 4/2006 | Rubbert et al. | 700/98 |
| 2006/0127836 A1 * | 6/2006 | Wen | 433/24 |
| 2006/0263739 A1 * | 11/2006 | Sporbert et al. | 433/24 |
| 2007/0003900 A1 * | 1/2007 | Miller | 433/24 |
| 2007/0072144 A1 * | 3/2007 | Imgrund et al. | 433/24 |
| 2007/0099147 A1 * | 5/2007 | Sachdeva et al. | 433/24 |

* cited by examiner

*Primary Examiner* — Cris L Rodriguez
*Assistant Examiner* — Matthew Nelson
(74) *Attorney, Agent, or Firm* — Wilson Sonsini Goodrich & Rosati

(57) ABSTRACT

The present invention relates to systems and methods of developing and tracking delivery and patient progression through an orthodontic treatment plan. One method includes identifying deviations from an orthodontic treatment plan, including receiving a digital representation of an actual arrangement of a patient's teeth after an orthodontic treatment plan has begun for the patient and prior to completion of the orthodontic treatment plan. The method further includes comparing the actual arrangement to a pre-determined planned arrangement to determine if the actual arrangement substantially deviates from the planned arrangement, the comparing comprising matching teeth from a previously segmented model to a surface of an unsegmented representation of the actual arrangement; and calculating one or more positional differences between the actual and planned arrangements of at least some of the corresponding teeth.

23 Claims, 11 Drawing Sheets

TREATMENT PROGRESS TRACKING AND RECALIBRATION

CROSS-REFERENCE

This application is a continuation of U.S. patent application Ser. No. 14/034,373, filed Sep. 23, 2013, which is a continuation of U.S. patent application Ser. No. 11/760,705, filed Jun. 8, 2007, now U.S. Pat. No. 8,562,338, issued Oct. 22, 2013, the entire contents of each of which are incorporated herein by reference.

This application is related to U.S. patent application Ser. No. 11/460,689, filed Jun. 8, 2007; U.S. patent application Ser. No. 11/760,701, filed Jun. 8, 2007; and U.S. patent application Ser. No. 11/760,612, filed Jun. 8, 2007, now U.S. Pat. No. 8,075,306, issued Dec. 13, 2011; the contents of each of which are incorporated herein by reference.

BACKGROUND OF THE INVENTION

The present invention relates generally to the field of orthodontics, and more particularly to systems and methods of developing and tracking delivery and patient progression through an orthodontic treatment plan.

An objective of orthodontics is to move a patient's teeth to positions where function and/or aesthetics are optimized. Traditionally, appliances such as braces are applied to the patient's teeth by an orthodontist or dentist and the set of braces exerts continual force on the teeth and gradually urges them toward their intended positions. Over time and with a series of clinical visits and adjustments to the braces, the orthodontist adjusts the appliances to move the teeth toward their final destination.

More recently, alternatives to conventional orthodontic treatment with traditional affixed appliances (e.g., braces) have become available. For example, systems including a series of preformed aligners have become commercially available from Align Technology, Inc., Santa Clara, Calif., under the tradename Invisalign® System. The Invisalign® System includes designing and/or fabricating multiple, and sometimes all, of the aligners to be worn by the patient before the aligners are administered to the patient and used to reposition the teeth (e.g., at the outset of treatment). Often, designing and planning a customized treatment for a patient makes use of computer-based 3-dimensional planning/design tools, such as ClinCheck® from Align Technology, Inc. The design of the aligners can rely on computer modeling of a series of planned successive tooth arrangements, and the individual aligners are designed to be worn over the teeth and elastically reposition the teeth to each of the planned tooth arrangements.

While patient treatment and tooth movements can be planned prospectively, in some cases orthodontic treatment can deviate from the planned treatment or stages. Deviations can arise for numerous reasons, and can include biological variations, poor patient compliance, and/or factors related to biomechanical design. In the case of aligners, continued treatment with previously designed and/or fabricated aligners can be difficult or impossible where a patient's teeth deviate substantially from the planned treatment course. For example, subsequent aligners may no longer fit the patient's teeth once treatment progression has deviated from the planned course. Because detecting a deviation from planned treatment most typically relies on visual inspection of the patient's teeth or observation of appliances no longer fitting, treatment can sometimes progress significantly off track by the time a deviation is detected, thereby making any required corrective measures more difficult and/or substantial. Earlier and better off track determinations would, therefore, be beneficial in order to recalibrate the fit of the aligner device on the teeth. Accordingly, improved methods and techniques of detecting and correcting treatment that has deviated from planned or desired treatment course would be desirable, particularly methods allowing early detection of treatment deviation.

SUMMARY OF THE INVENTION

The present invention provides improved systems and methods for tracking a patient's progress according to a planned treatment, incorporating enhanced tracking techniques into treatment delivery and management, and, if necessary, revising or modifying the patient's treatment plan based on a determination that treatment has progressed off track. Information obtained according to the invention techniques can be used, for example, to more actively and/or effectively manage delivery of orthodontic treatment, increasing treatment efficacy and successful progression to the patient's teeth to the desired finished positions.

Thus, in one aspect, the present invention includes systems and methods of identifying deviations from an orthodontic treatment plan. A method can include, for example, receiving a digital representation of an actual arrangement of a patient's teeth after an orthodontic treatment plan has begun for the patient and prior to completion of the orthodontic treatment plan; and comparing the actual arrangement to a pre-determined planned arrangement to determine if the actual arrangement substantially deviates from the planned arrangement, and calculating one or more positional differences between the actual and planned arrangements of at least some of the corresponding teeth.

The present invention further includes systems and methods of managing delivery and patient progression through an orthodontic treatment plan. Such a method can include, for example, providing an initial treatment plan for a patient, providing a set of orthodontic appliances, tracking progression of the patient's teeth along the treatment path, comparing the actual arrangement with a planned arrangement to determine if the actual arrangement of the teeth matches a planned tooth arrangement, and generating a revised treatment plan where it is determined that the actual tooth arrangement deviates from the planned tooth arrangement. In another example, a method can include receiving a digital representation of an actual arrangement of a patient's teeth after an orthodontic treatment plan has begun for the patient and prior to completion of the orthodontic treatment plan; comparing the actual arrangement to a digital model of a planned arrangement, and generating a revised treatment plan.

A system can include a computer coupled to a server, the computer comprising a processor and a computer readable medium comprising instructions which, if executed, cause the computer to: receive a digital representation of an actual arrangement of a patient's teeth after the orthodontic treatment plan has begun for the patient and prior to completion of the orthodontic treatment plan; compare the actual arrangement to a pre-determined planned arrangement; and calculate one or more positional differences between the actual and planned arrangements of at least some of the corresponding teeth; and generate a revised treatment plan.

A system according to another embodiment of the present invention can include a computer coupled to a server, the computer comprising a processor and a computer readable medium comprising instructions which, if executed, cause the computer to generate an initial treatment plan for a patient including enhanced tracking of the patient's treatment progress, provide a set of orthodontic appliances corresponding to a treatment phase, track progression of the patient's teeth along a treatment path, compare the actual arrangement with a planned arrangement, and generate a revised treatment plan where it is determined that the actual tooth arrangement substantially deviates from the planned tooth arrangement.

For a fuller understanding of the nature and advantages of the present invention, reference should be made to the ensuing detailed description and accompanying drawings. Other aspects, objects and advantages of the invention will be apparent from the drawings and detailed description that follows.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
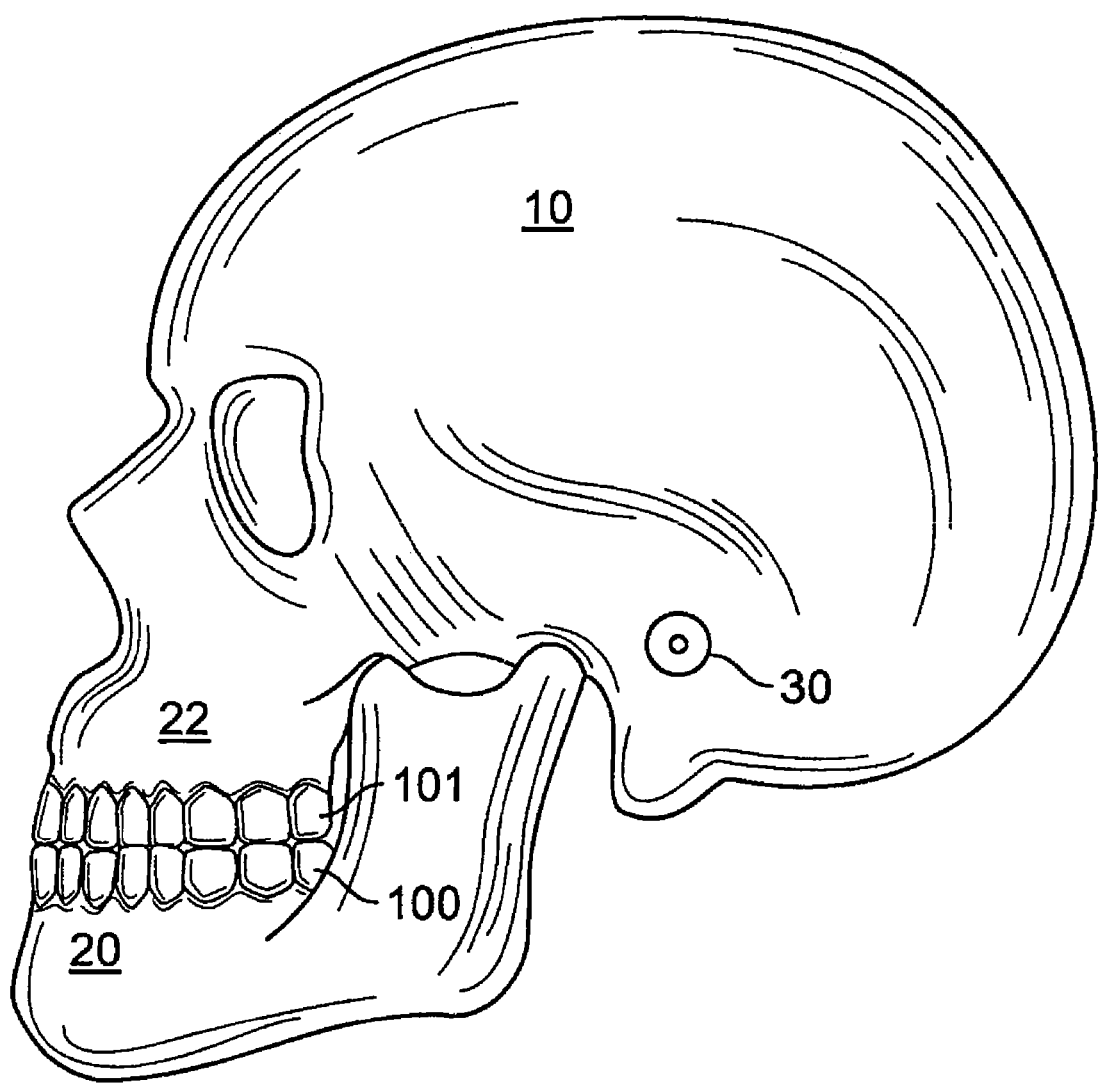
FIG. 1 is a diagram showing the anatomical relationship of the jaws of a patient.

The invention described herein provides improved systems and methods for tracking a patient's progress according to a planned treatment, incorporating enhanced tracking techniques into treatment delivery and management, and, if necessary, revising or modifying the patient's treatment plan based on a determination that treatment has progressed off track. Systems and methods of treatment progress tracking and revised planning can be included in a variety of orthodontic treatment regimens. For example, the progress tracking and revised planning features can be optionally included and incorporated into other aspects of treatment according to the Invisalign® System. Treatment can be pre-planned for administering to a patient in a series of one or more phases, with each phase including a set of appliances that are worn successively by the patient to reposition the teeth through planned arrangements and eventually toward a selected final arrangement. Progress tracking, according to the present invention, is incorporated into the pre-planned treatment for monitoring and management, and to provide enhanced detection and feedback as to whether treatment is progressing on track.

Tracking can occur at any point during treatment but will typically be scheduled to correspond with a patient completing a pre-planned phase of treatment (e.g., wearing each appliance in a designated set). For example, once initial staging of a patients teeth is completed (e.g., model initial, intermediate, and final teeth arrangements) and a treatment plan has been devised, a dental practitioner can be sent a first set of one or more appliances to be administered to the patient in the first phase of treatment. After the last appliance in the first set is administered to the patient, an image of the patient's teeth in their positions following administration of the first set of appliances can be taken (e.g., scan, impression, etc.). From the image of the patient's teeth in their current position, an assessment is made as to how the treatment is tracking relative to the original treatment projections. If there is a substantial deviation from the planned treatment path, then corrective action can be taken, for example, in order to achieve the original designed final position. Treatment then progresses to the next phase, where treatment is either finalized if the intended final positions are reached, or a second set of appliances can be sent to the practitioner for administration to the patient. The second set of appliances can be based on the initial treatment plan if treatment is progressing on track, or can be based on a revised or modified treatment plan where a determination is made that treatment is off track.

Methods and techniques for tracking and preserving the original final position in the treatment is generally referred to herein as "teeth matching" or "bite matching". For example, bite matching techniques described herein can include matching teeth from the original image of the teeth or impression, to surface(s) of a new model of the teeth taken after treatment has begun. An off-track determination can be followed by "re-setting" to the actual position of the teeth as defined by data represented in the progress scan, the original data of the teeth (i.e., segmented models from initial treatment plan), thereby allowing preservation of the initially selected final target position of the teeth. In other words, the original data set which contains with it, an established target arrangement, can be reused, by repositioning the teeth arrangement according to the positions of the (same) teeth captured in the progress scan. In so doing, a new planned path to go from the current to the target can be recreated without having to change the original target configuration. This method is enabled by using bite matching techniques to allow the current aligner geometry to be recalibrated and reshaped according to the actual position of the teeth in the progress scan. Using such bite matching techniques provides significant advantages in terms of efficiency as there is no need to re-segment and process the new scan of the teeth, and in terms of efficacy since the initial final arrangement is preserved, even if the patient progresses off track.

Incorporating the inventive techniques and tracking methods described herein in managing delivery/modification would provide various advantages, including earlier detection of treatment deviations, allowing earlier remedial measures to be taken, if necessary, to avoid undesirable treatment outcomes and preservation of initial treatment goals, thereby ultimately allowing for more effective treatment and better clinical outcomes. Furthermore, treatment efficiency and efficacy can be increased by better avoidance of inefficient/undesirable treatment "detours". Additionally, improved monitoring and tracking, as described, is more objective and reliable, and less qualitative in nature than the common practice of visually identifying off-track progress. This reduces the inter-clinician variability and reduces the dependency of accurate detection on clinician experience. As such, currently described inventive methods and techniques can inspire more confidence in both patients and practitioners, including practitioners that may be less experienced with a given treatment method and/or less confident in their abilities to clinically detect off-track progression, or even more experienced practitioners who desire more detailed monitoring, for example, in cases involving more difficult or less predictable movements.

FIG. 1 shows a skull 10 with an upperjaw bone 22 and a lowerjaw bone 20. The lowerjaw bone 20 hinges at a joint 30 to the skull 10. The joint 30 is called a temporal mandibular joint (TMJ). The upperjaw bone 22 is associated with an upper jaw 101, while the lower jaw bone 20 is associated with a lower jaw 100. A computer model of the jaws 100 and 101 is generated, and a computer simulation models interactions among the teeth on the jaws 100 and 101. The computer simulation allows the system to focus on motions involving contacts between teeth mounted on the jaws. The computer simulation allows the system to render realistic jaw movements that are physically correct when the jaws 100 and 101 contact each other. The model of the jaw places the individual teeth in a treated position. Further, the model can be used to simulate jaw movements including protrusive motions, lateral motions, and "tooth guided" motions where the path of the lower jaw 100 is guided by teeth contacts rather than by anatomical limits of the jaws 100 and 101. Motions are applied to one jaw, but may also be applied to both jaws. Based on the occlusion determination, the final position of the teeth can be ascertained.

Figure 2A:
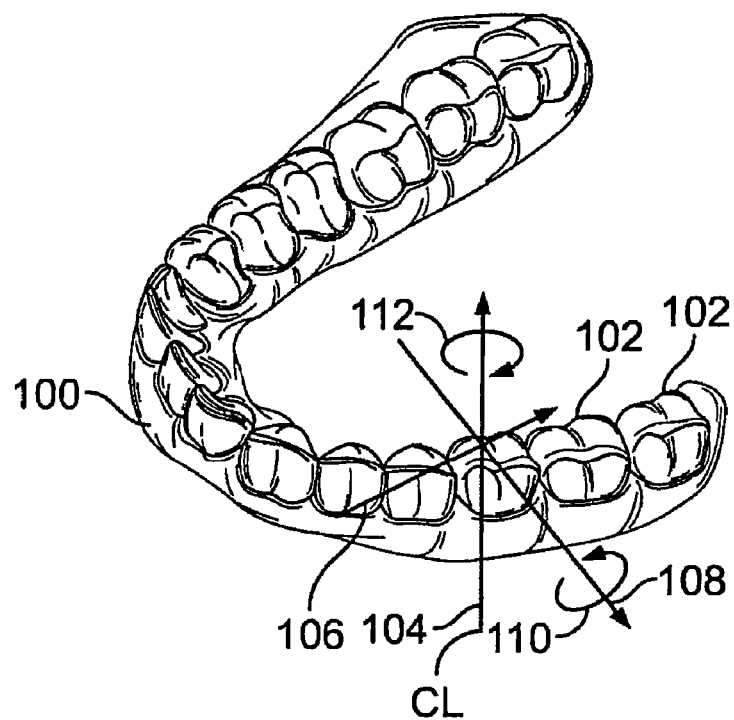
FIG. 2A illustrates in more detail the patient's lower jaw and provides a general indication of how teeth may be moved according to an embodiment of the present invention.

Referring now to FIG. 2A, the lower jaw 100 includes a plurality of teeth 102, for example, At least some of these teeth may be moved from an initial tooth arrangement to a final tooth arrangement. As a frame of reference describing how a tooth may be moved, an arbitrary centerline (CL) may be drawn through the tooth 102. With reference to this centerline (CL), each tooth may-be moved in orthogonal directions represented by axes 104, 106, and 108 (where 104 is the centerline). The centerline may be rotated about the axis 108 (root angulation) and the axis 104 (torque) as indicated by arrows 110 and 112, respectively. Additionally, the tooth may be rotated about the centerline, as represented by an arrow 112. Thus, all possible free-form motions of the tooth can be performed.

Figure 2B:
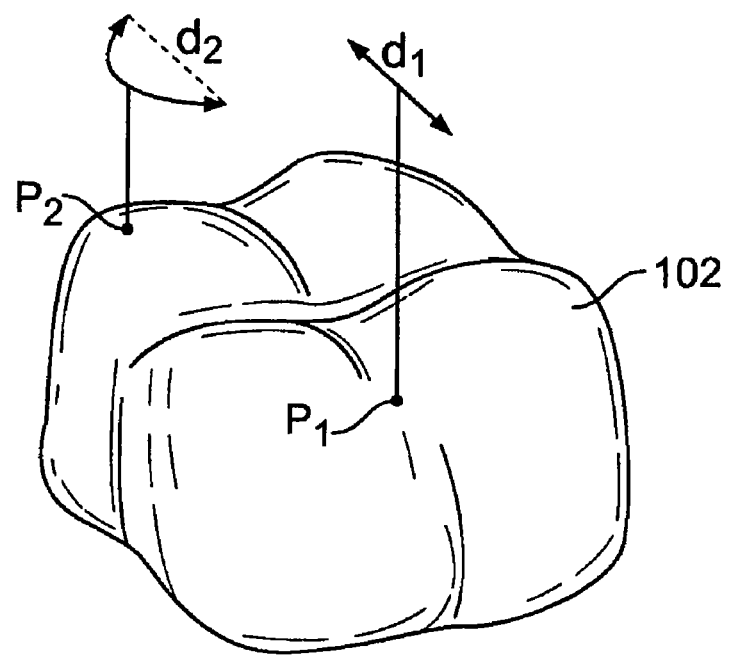
FIG. 2B illustrates a single tooth from FIG. 2A and defines determination of tooth movement distance according to an embodiment of the present invention.

FIG. 2B shows how the magnitude of any tooth movement may be defined in terms of a maximum linear translation of any point P on a tooth 102. Each point P1 will undergo a cumulative translation as that tooth is moved in any of the orthogonal or rotational directions defined in FIG. 2A. That is, while the point will usually follow a nonlinear path, there is a linear distance between any point in the tooth when determined at any two times during the treatment. Thus, an arbitrary point P1 may in fact undergo a true side-to-side translation as indicated by arrow d1, while a second arbitration point P2 may travel along an accurate path, resulting in a final translation d2. Many aspects of the present invention are defined in terms of the maximum permissible movement of a point P1 induced on any particular tooth. Such maximum tooth movement, in turn, is defined as the maximum linear translation of that point P1 on the tooth that undergoes the maximum movement for that tooth in any treatment step.

Figure 2C:
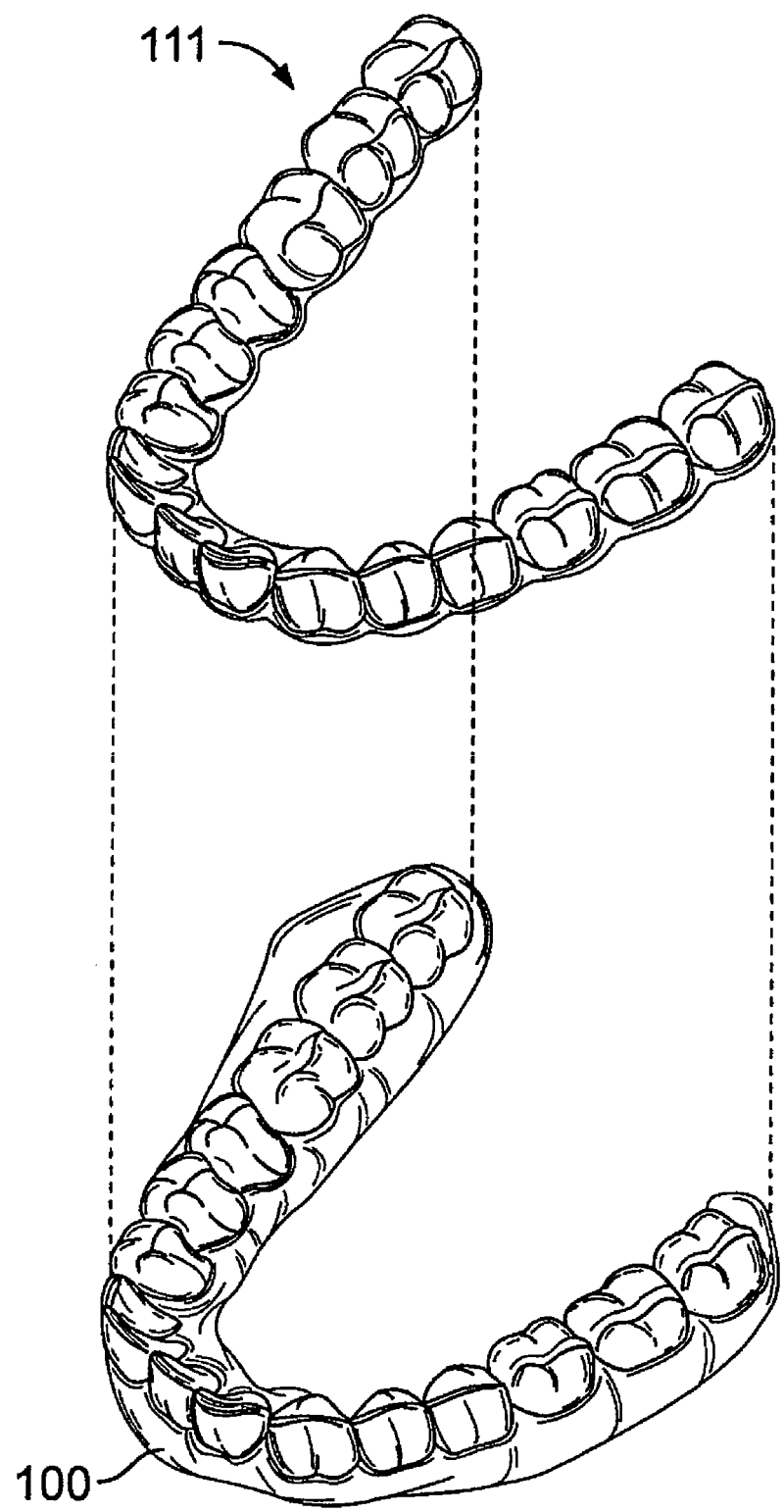
FIG. 2C illustrates the jaw of FIG. 2A together with an incremental positioning adjustment appliance according to an embodiment of the present invention.

FIG. 2C shows one adjustment appliance 111 which is worn by the patient in order to achieve an incremental repositioning of individual teeth in the jaw as described generally above. The appliance can include a shell (e.g., polymeric shell) having teeth-receiving cavities that receive and resiliently reposition the teeth. Such appliances, including those utilized in the Invisalign® System, are described in numerous patents and patent applications assigned to Align Technology, Inc. including, for example in U.S. Pat. Nos. 6,450,807, and 5,975,893, as well as on the company's website, which is accessible on the World Wide Web (see, e.g., the url "align.com").

As set forth in the prior applications, each appliance may be configured so that its tooth-receiving cavity has a geometry corresponding to an intermediate or final tooth arrangement intended for the appliance. The patient's teeth are progressively repositioned from their initial tooth arrangement to a final tooth arrangement by placing a series of incremental position adjustment appliances over the patient's teeth. The adjustment appliances can be generated all at the same stage or in sets or batches, e.g., at the beginning of a stage of the treatment, and the patient wears each appliance until the pressure of each appliance on the teeth can no longer be felt or has resulted in the maximum allowable tooth movement for that given stage. A plurality of different appliances (e.g., set) can be designed and even fabricated prior to the patient wearing any appliance of the plurality. At that point, the patient replaces the current appliance with the next appliance in the series until no more appliances remain. The appliances are generally not affixed to the teeth and the patient may place and replace the appliances at any time during the procedure. The final appliance or several appliances in the series may have a geometry or geometries selected to overcorrect the tooth arrangement, i.e., have a geometry which would (if fully achieved) move individual teeth beyond the tooth arrangement which has been selected as the "final." Such over-correction may be desirable in order to offset potential relapse after the repositioning method has been terminated, i.e., to permit movement of individual teeth back toward their pre-corrected positions. Over-correction may also be beneficial to speed the rate of correction, i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance.

Figure 3:
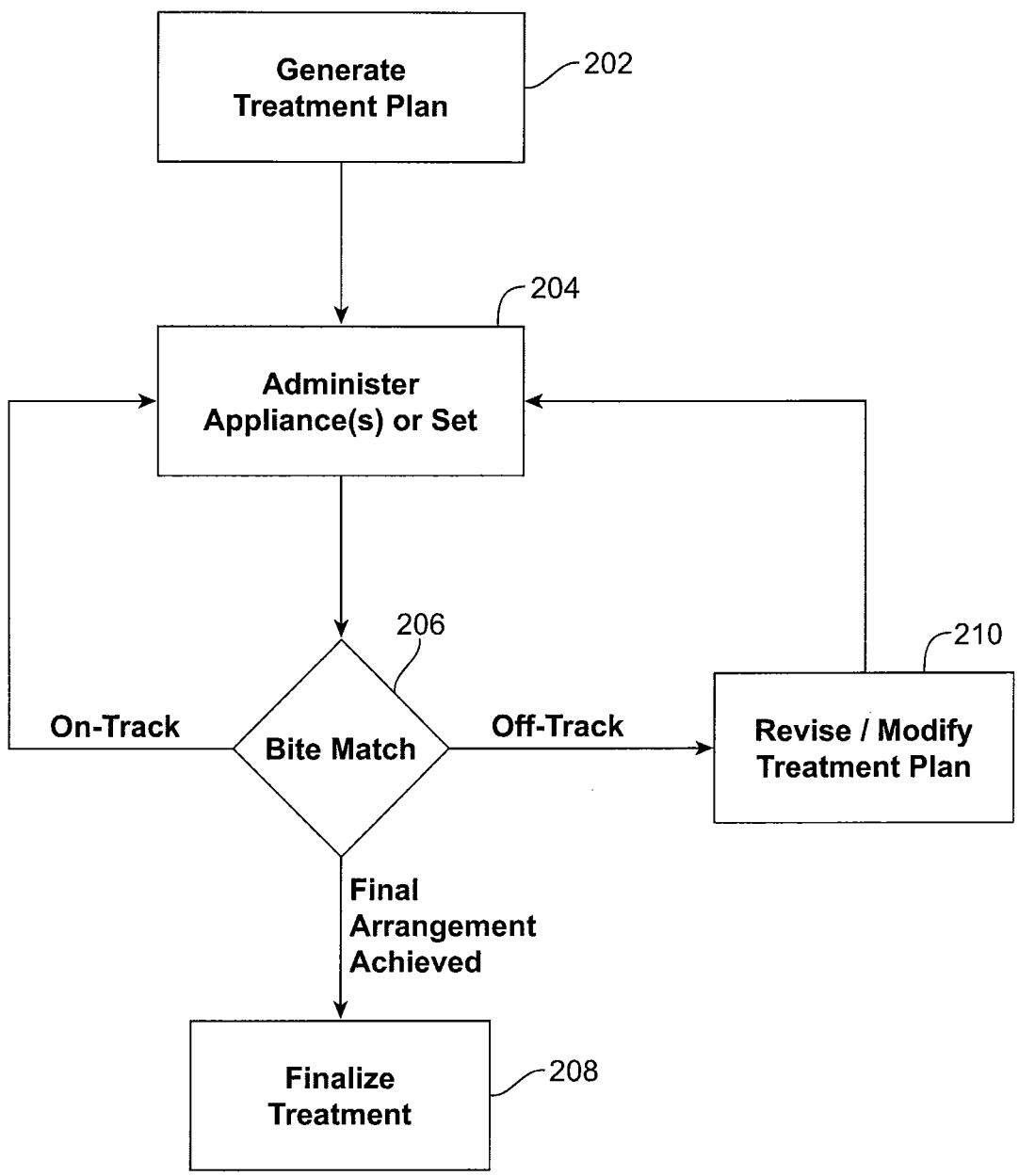
FIG. 3 shows generating and administering treatment according to an embodiment of the present invention.

Referring to FIG. 3, a method 200 according to the present invention is illustrated. Individual aspects of the process are discussed in further detail below. The process includes generating a treatment plan for repositioning a patient's teeth (Step 202). Briefly, a treatment plan will include obtaining data comprising an initial arrangement of the patient's teeth, which typically includes obtaining an impression or scan of the patient's teeth prior to the onset of treatment. The treatment plan will also include identifying a final or target arrangement of the patient's teeth that is desired, as well as a plurality of planned successive or intermediary tooth arrangements for moving the teeth along a treatment path from the initial arrangement toward the selected final or target arrangement. Appliances can be generated based on the planned arrangements and administered to the patient (Step 204). The appliances are typically administered in sets or batches of appliances, such as sets of 2, 3, 4, 5, 6, 7, 8, 9, or more appliances, but are not limited to any particular administrative scheme. After the treatment plan begins and following administration of appliances to the patient, teeth matching is done to assess a current and actual arrangement of the patient's teeth compared to a planned arrangement (Step 206). If the patient's teeth are determined to be "on-track" and progressing according to the treatment plan, then treatment progresses as planned. If the patient's teeth have reached the initially planned final arrangement, then treatment progresses to the final stages of treatment (Step 208). Where the patient's teeth are determined to be tracking according to the treatment plan, but have not yet reached the final arrangement, the next set of appliances can be administered to the patient (repeat Step 204, according to the initial Treatment Plan). If, on the other hand, the patient's teeth are determined at the teeth matching step (Step 206) not to be tracking with the treatment plan, then treatment is characterized as "off-track" and an assessment is made as to how further treatment of the patient will proceed. Typically, a revised treatment plan will be generated (Step 210), and may be selected, for example, to reposition the teeth from the current position to a final position, which may be the same destination as the initially determined final position according to the initial treatment plan.

Systems of the present invention can include network based systems, including a data network and a server terminal operatively coupled to the network. One or more client terminals can be included and operatively coupled to the network. Systems can optionally include more stand-alone or non-network based systems, including computers and software packages designed to at least partially operate independent of a data network and in which various steps of the currently described methods can be accomplished in an automated fashion at a remote location (e.g., practitioner's office).

Figure 4:
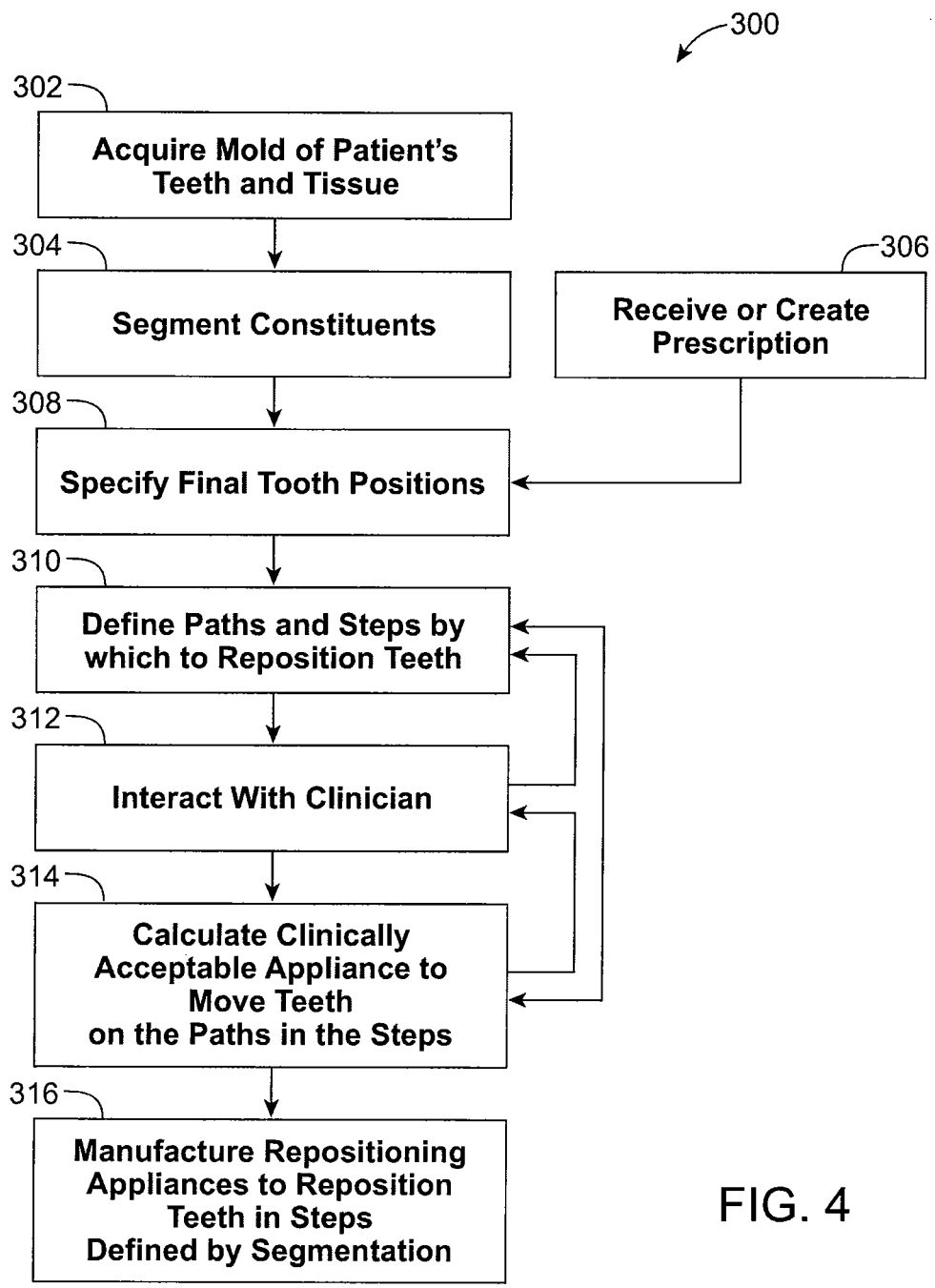
FIG. 4 illustrates generating a treatment plan according to an embodiment of the present invention.

FIG. 4 illustrates the general flow of an exemplary process 300 for defining and generating a treatment plan, including repositioning appliances for orthodontic treatment of a patient. The process 300 includes the methods, and is suitable for the apparatus, of the present invention, as will be described. The steps of the process can be implemented as computer program modules for execution on one or more computer systems.

As an initial step, a mold or a scan of patient's teeth or mouth tissue is acquired (Step 302). This generally involves taking casts of the patient's teeth and gums, and may in addition or alternately involve taking wax bites, direct contact scanning, x-ray imaging, tomographic imaging, sonographic imaging, and other techniques for obtaining information about the position and structure of the teeth, jaws, gums and other orthodontically relevant tissue. From the data so obtained, a digital data set is derived that represents an initial (e.g., pretreatment) arrangement of the patient's teeth and other tissues.

The initial digital data set, which may include both raw data from scanning operations and data representing surface models derived from the raw data, is processed to segment the tissue constituents from each other (Step 304), including defining discrete dental objects. For example, data structures that digitally represent individual tooth crowns can be produced. In some embodiments, digital models of entire teeth are produced, including measured or extrapolated hidden surfaces and root structures.

Desired final position of the teeth, or tooth positions that are desired and/or intended end result of orthodontic treatment, can be received, e.g., from a clinician in the form of a descriptive prescription, can be calculated using basic orthodontic prescriptions, or can be extrapolated computationally from a clinical prescription (Step 306). With a specification of the desired final positions of the teeth and a digital representation of the teeth themselves, the final position and surface geometry of each tooth can be specified (Step 308) to form a complete model of the teeth at the desired end of treatment. The result of this step is a set of digital data structures that represents a desired and/or orthodontically correct repositioning of the modeled teeth relative to presumed-stable tissue. The teeth and surrounding tissue are both represented as digital data.

Having both a beginning position and a final target position for each tooth, the process next defines a treatment path or tooth path for the motion of each tooth (Step 310). This includes defining a plurality of planned successive tooth arrangements for moving teeth along a treatment path from an initial arrangement to a selected final arrangement. In one embodiment, the tooth paths are optimized in the aggregate so that the teeth are moved in the most efficient and clinically acceptable fashion to bring the teeth from their initial positions to their desired final positions.

At various stages of the process, the process can include interaction with a clinician responsible for the treatment of the patient (Step 312). Clinician interaction can be implemented using a client process programmed to receive tooth positions and models, as well as path information from a server computer or process in which other steps of process 300 are implemented. The client process is advantageously programmed to allow the clinician to display an animation of the positions and paths and to allow the clinician to reset the final positions of one or more of the teeth and to specify constraints to be applied to the segmented paths.

The tooth paths and associated tooth position data are used to calculate clinically acceptable appliance configurations (or successive changes in appliance configuration) that will move the teeth on the defined treatment path in the steps specified (Step 314). Each appliance configuration corresponds to a planned successive arrangement of the teeth, and represents a step along the treatment path for the patient. The steps are defined and calculated so that each discrete position can follow by straight-line tooth movement or simple rotation from the tooth positions achieved by the preceding discrete step and so that the amount of repositioning required at each step involves an orthodontically optimal amount of force on the patient's dentition. As with other steps, this calculation step can include interactions with the clinician (Step 312).

Having calculated appliance definitions, the process 300 can proceed to the manufacturing step (Step 316) in which appliances defined by the process are manufactured, or electronic or printed information is produced that can be used by a manual or automated process to define appliance configurations or changes to appliance configurations. Appliances according to the treatment plan can be produced in entirety, such that each of the appliances are manufactured (e.g., prior to treatment), or can be manufactured in sets or batches. For example, in some cases in might be appropriate to manufacture an initial set of appliances at the outset of treatment with the intention of manufacturing additional sets of appliances (e.g., second, third, fourth, etc.) after treatment has begun (e.g., as discussed further herein). For example, a first set of appliances can be manufactured and administered to a patient. Following administration, it may be desirable to track the progression of the patient's teeth along the treatment path before manufacturing and/or administering subsequent set(s) of appliances.

Generating and/or analyzing digital treatment plans, as discussed herein, can include, for example, use of 3-dimensional orthodontic treatment planning tools such as ClinCheck from Align Technology, Inc. or other software available from eModels and OrthoCAD, among others. These technologies allow the clinician to use the actual patient's dentition as a starting point for customizing the treatment plan. The ClinCheck technology uses a patient-specific digital model to plot a treatment plan, and then uses a processed (e.g., segmented) scan of the achieved treatment outcome to assess the degree of success of the outcome as compared to the original digital treatment plan as, as discussed in U.S. Pat. Nos. 7,156,661 and 7,077,647 (see also, below).

In some cases, patients do not progress through treatment as expected and/or planned. For example, in some instances a patient's progression along a treatment path can become "off-track" or will deviate from an initial treatment plan, whereby an actual tooth arrangement achieved by the patient will differ from the expected or planned tooth arrangement, such as a planned tooth arrangement corresponding to the shape of a particular appliance. A determination that the progression of a patient's teeth is deviating or not tracking with the original treatment plan can be accomplished in a variety of ways. As set forth above, off-track deviations can be detected by visual and/or clinical inspection of the patient's teeth. For example, a substantial off track deviation from the expected or planned treatment may become apparent when the patient tries to wear a next appliance in a series. If the actual tooth arrangement substantially differs from the planned arrangement of the teeth, the next appliance will typically not be able to seat properly over the patient's teeth. Thus, an off-track deviation may become substantially visually apparent to a treating professional, or even to the patient, upon visual or clinical inspection of the teeth.

Detecting deviations from a planned treatment, however, can be difficult, particularly for patients as well as certain dental practitioners, such as those with more limited experience in orthodontics, certain general dentist, technicians and the like. Additionally, deviations that have progressed to the point that they are visually detectable clinically are often substantially off track with respect to the planned treatment, and earlier means of off-track detection is often desired. Thus, detecting deviations from a treatment plan can also be accomplished by comparing digital models of the patients teeth, and can often detect deviations from a treatment plan before the deviation becomes substantially apparent by visual or clinical inspection.

Figure 5:
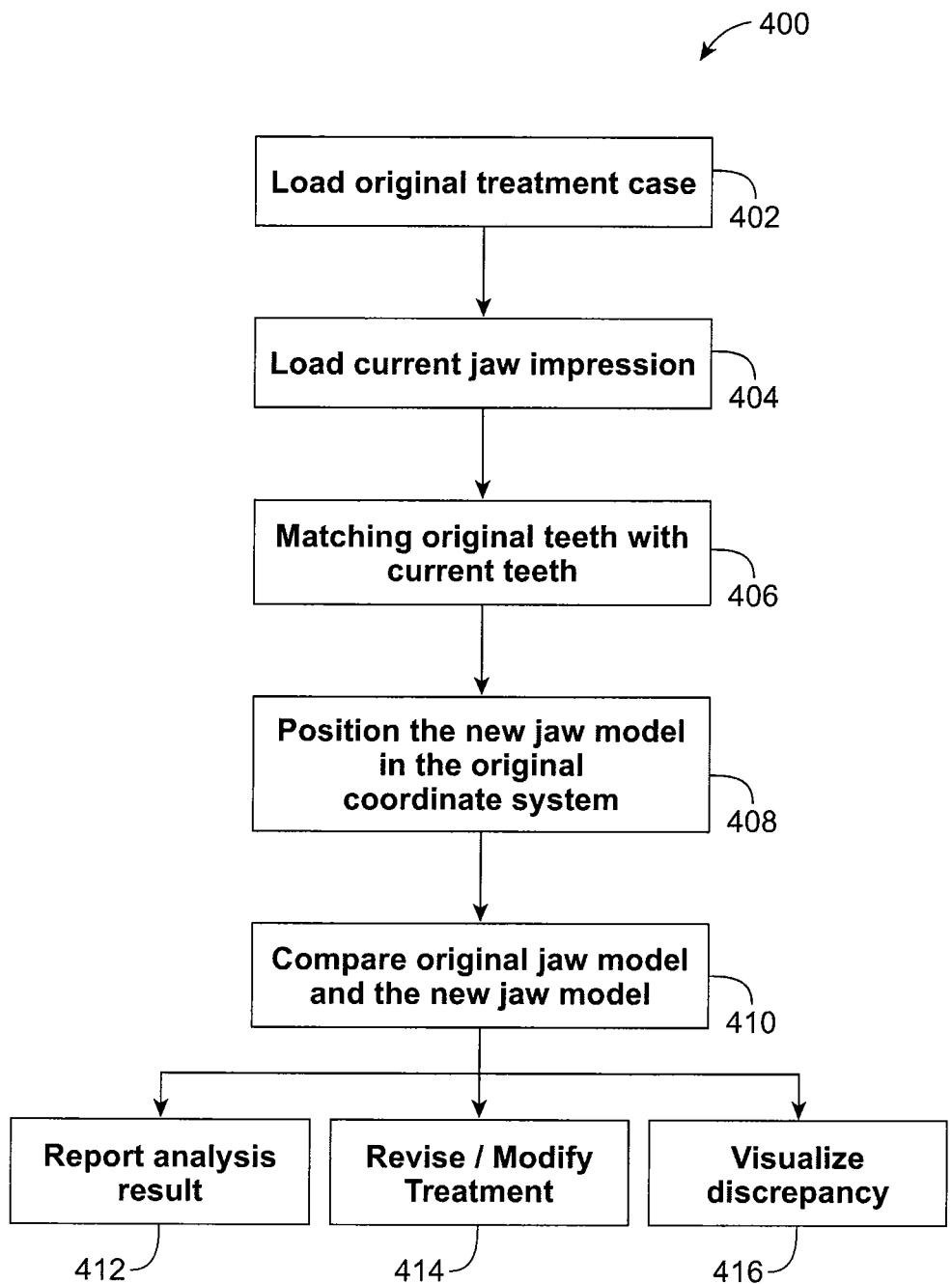
FIG. 5 illustrates a process including teeth matching according to one embodiment of the present invention.

An exemplary computer based teeth matching process according to an embodiment of the present invention is described with reference to FIG. 5. First, data from an earlier treatment plan is received (Step 402). Typically, data includes the initial data set or image data representing the patient's teeth in the original, pre-treatment positions, the initially identified final position, as well as planned intermediate or successive arrangements selected for moving teeth along the initial treatment path from the initial arrangement to the selected final arrangement. Next, a current jaw impression or data including a digital representation of the teeth in their current positions, after treatment has begun, is received and loaded (Step 404). Data including planned arrangements of the teeth are then compared to data including a representation of the patient's teeth in their current positions for an initial determination of whether a match exists (Step 406). Next, the new jaw data is segmented and positioned in the original coordinate system (Step 408). The process then compares the original jaw data against the new jaw data (Step 410). Based on the comparison, the process generates an analysis report (Step 412), new/revised treatment options or plans (Step 414), and/or allows visualization of any detected discrepancy (Step 416). See also, e.g., U.S. Pat. Nos. 7,156,661 and 7,077,647, for discussion of comparing actual position of the teeth relative to a planned or expected position using a processed (e.g., segmented) scan of the teeth positions following initiation of treatment.

In some instances, detecting a deviation from a treatment plan via comparison between digital models of the patients teeth can include comparing a current scan or image, which has not been segmented, of the patients teeth in a position after treatment has begun to a previously segmented data set of the patients teeth at a current, past or future stage. Use of an unsegmented, rather than segmented, digital representation of the current teeth positions may be desirable, for example, in order to avoid resource and/or labor intensive processing steps to transform the current unsegmented digital teeth model to a segmented digital teeth model. In addition, lower resolution or quality scans or images can save cost and time if the necessary reference points can be identified on the unsegmented current scan or image.

Figure 6:
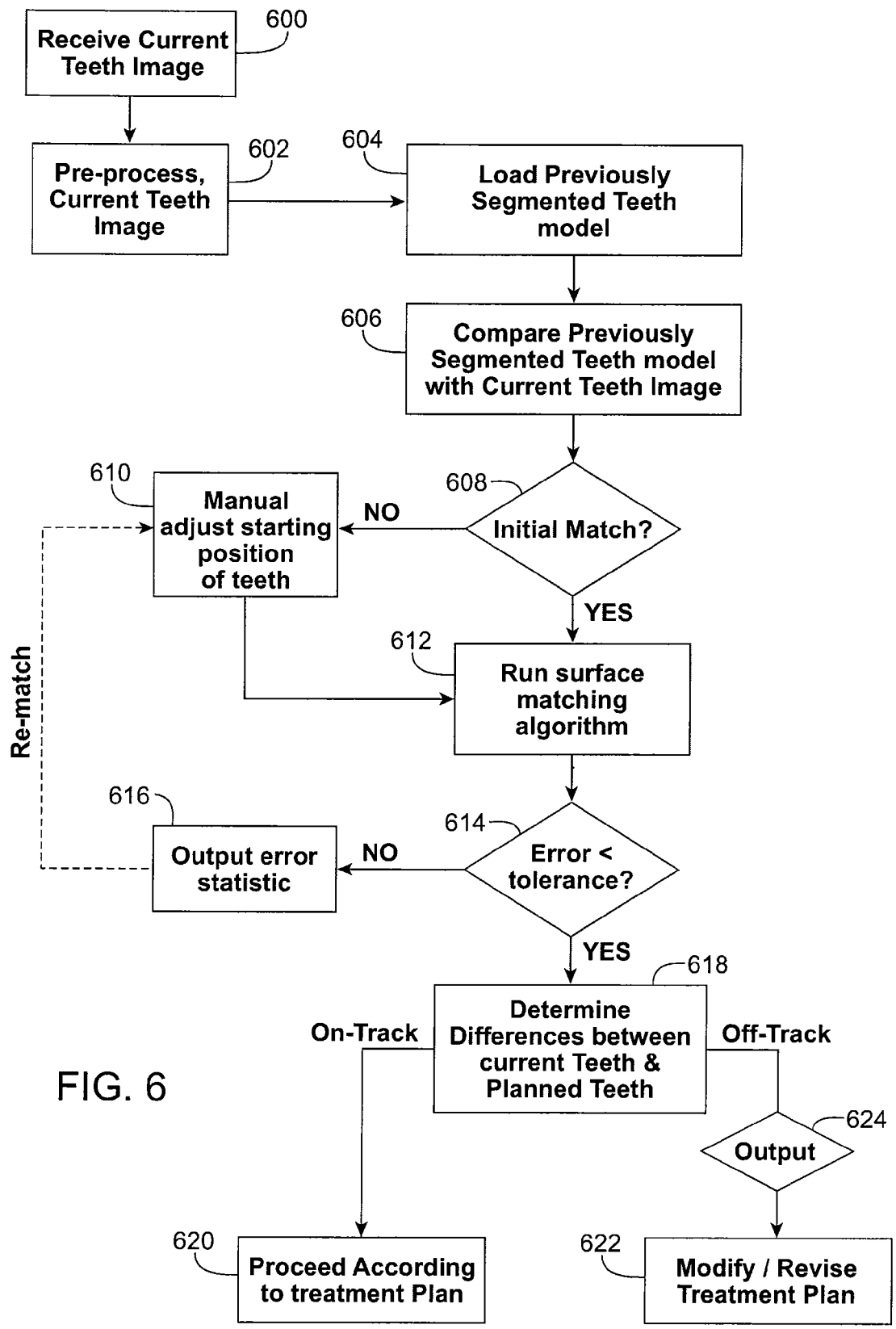
FIG. 6 shows a process including teeth matching according to another embodiment of the present invention.

FIG. 6 is a flow chart showing the steps of correcting deviations from a planned course of treatment to gradually reposition teeth, according to one embodiment of the present disclosure. The process starts in step 600, when current jaw data or "Current Teeth Image" is received. The current jaw data includes data representing an actual arrangement of the patients teeth following administration of appliances according to the original treatment plan. In step 602, the Current Teeth Image is pre-processed using a digital data tool (DDT) such that each tooth is assigned a Facial Axis of the Clinical Crown (FACC), i.e. a unique current identifier, with jaw characteristics set. Typically, according to the described embodiment, the Current Teeth Image does not need to be segmented, which saves a technician's time and hence overall cost.

In step 604, a Previously Segmented Teeth Model is selected, and is input into a system of the present invention for analysis and comparison with the Current Teeth Image. The Previously Segmented Teeth Model selected can include an Initially Segmented Teeth Model or a digital model of the patient's teeth in their initial, pre-treatment positions, the initial final position according to the initial or previous treatment plan (e.g., Prescribed Tooth Arrangement), or a planned successive tooth arrangement therebetween.

In step 606, the Previously Segmented Teeth Model and the Current Teeth Image are compared. This step includes a sort of "rough match" of the segmented model and the Current Teeth Image to identify corresponding features of the two models that may be compared (Step 608). For example, an initial matching algorithm can be executed which matches unique starting identifiers (FACCs) of each tooth in the Previously Segmented Teeth Model to the respective unique current identifiers (FACCs) of each tooth in the Current Teeth Image. The images can be overlaid on each other and the relative location of each tooth identified by its unique identifier (or FACC) to determine if there are any mismatches in step 608.

If any mismatches are found, an initial match has not occurred and the mismatches are displayed in the form of an informational dialog that provides details of the mismatches, such as teeth numbering irregularities or missing FACCs. A mismatch can occur, for example, if there are any teeth numbering irregularities, such as the total number of teeth in each model is not the same, or at least one tooth is missing a FACC. Mismatches may result, for example, where substantial dental work or reconstruction (e.g., tooth extraction, tooth reconstruction, filling, etc.) has occurred following the initial treatment plan or generation of Previously Segmented Teeth Model.

In Step 610, initial mismatch errors as identified above can be manually accounted for in the process. For example, a technician can manually adjust or reposition each tooth with a mismatch using the Previously Segmented Teeth Model or adjusts the information relating to each tooth with a mismatch (e.g., accounting for an extracted tooth).

If no mismatches are generated in step 608, or where mismatches have been accounted for according to 610, then an initial match occurs and the process moves to step 612. The initial match confirms that the technician is using the correct Previously Segmented Teeth Model and the Current Teeth Image, which provides a good starting point for executing a surface matching algorithm.

In step 612, more detailed matching and comparison between Previously Segmented Teeth Model and the Current Teeth Image occurs, which includes execution a surface matching algorithm. The surface matching algorithm can take a number of samples of each tooth in the Previously Segmented Teeth Model and finds the closest corresponding sampling point on the Current Teeth Image. A grid is created on each tooth and the number of samples is randomly selected and then the grid is overlaid on the Current Teeth Image.

In step 614, any resulting errors from the surface matching algorithm are compared to predetermined tolerances to determine if the resulting errors are less than the predetermined tolerance. Error tolerances can account for potential differences in the models being compared that might impair meaningful comparison, such as errors due to typical variance between different scans or impressions, surface differences or fluctuations, and the like. If the resulting errors are greater than the pre-determined tolerance, then in step 616, error statistics for the surface matching algorithm are typically output to a display device and can be further redirected to a technician for manual input or correction as in step 610.

If the resulting errors are less than the pre-determined tolerance, in step 618, then matching and comparison of the Previously Segmented Teeth Model and the Current Teeth Image proceeds for a determination whether the actual arrangement of the patient's teeth deviates from the planned arrangement. In particular, a determination can be made as to whether positional differences exist, and to what degree, between the teeth in their current positions compared to the expected or planned positions. Positional differences may indicate whether the patient's teeth are progressing according to the treatment plan or if the patient's teeth are substantially off track. Various clinical and/or positional parameters can be examined and compared for a determination as to whether a patient's teeth are substantially on track or are deviating from an expected arrangement according to the treatment plan. For example, positional parameters examined can include tooth rotation, extrusion, intrusion, angulation, inclination, translation, and the like. Threshold values for differences in one or more positional parameters can be selected as being indicative of a significant or substantial difference in tooth position. Exemplary threshold values for various positional parameters, according to one embodiment of the invention are listed in Table 1 below. Detecting positional differences above the selected threshold value(s) indicates that the actual arrangement of the patients teeth substantially deviates from the planned arrangement to which the comparison is made.

TABLE 1

OFF TRACK PARAMETERS. The threshold difference values of a planned position of teeth to actual positions selected as indicating that a patient's teeth have progressed substantially off-track.

| Type Movement | Difference Actual/Planned |
|---|---|
| Rotations | |
| Upper central incisors | 9 deg |
| Upper lateral incisors | 11 deg |
| Lower incisors | 11 deg |
| Upper cuspids | 11 deg |
| Lower cuspids | 9.25 deg |
| Upper Bicuspids | 7.25 deg |
| Lower First Bicuspid | 7.25 deg |
| Lower Second Bicuspid | 7.25 deg |
| molars | 6 deg |
| Extrusion | |
| Anterior | 0.75 mm |
| Posterior | 0.75 mm |
| Intrusion | |
| Anterior | 0.75 mm |
| Posterior | 0.75 mm |
| Angulation | |
| Anterior | 5.5 deg |
| Posterior | 3.7 deg |
| Inclination | |
| Anterior | 5.5 deg |
| Posterior | 3.7 deg |
| Translation | |
| BL Anterior | 0.7 mm |
| BL Posterior Cuspids | 0.9 mm |
| MD Anterior | 0.45 mm |
| MD Cuspids | 0.45 mm |
| MD Posterior | 0.5 mm |

If the patient's teeth are determined to be on track by comparison of the teeth in their current positions with teeth in their expected or planned positions, then treatment can progress according to the existing or original treatment plan (Step 620). For example, a patient determined to be progressing on track can be administered one or more subsequent appliances according to the treatment plan, such as the next set of appliances. Treatment can progress to the final stages and/or can reach a point in the treatment plan where bite matching is repeated for a determination of whether the patient's teeth are progressing as planned or if the teeth are off track. If the patient's teeth are determined off track and deviating from the planned arrangement, then treatment according to the original treatment plan will be suspended. Typically, a modified or revised treatment plan will be generated where a patient's teeth are determined as being substantially off track (Step 622). Regardless of whether the patient's teeth are determined to be off track or progressing according to the treatment plan, the process can generate a report or analysis of the results, and/or visualize the comparison, including any detected discrepancy (Step 624). Any such product can be transmitted, for example, to a technician or treating professional, to the patient, or elsewhere.

Figure 7:
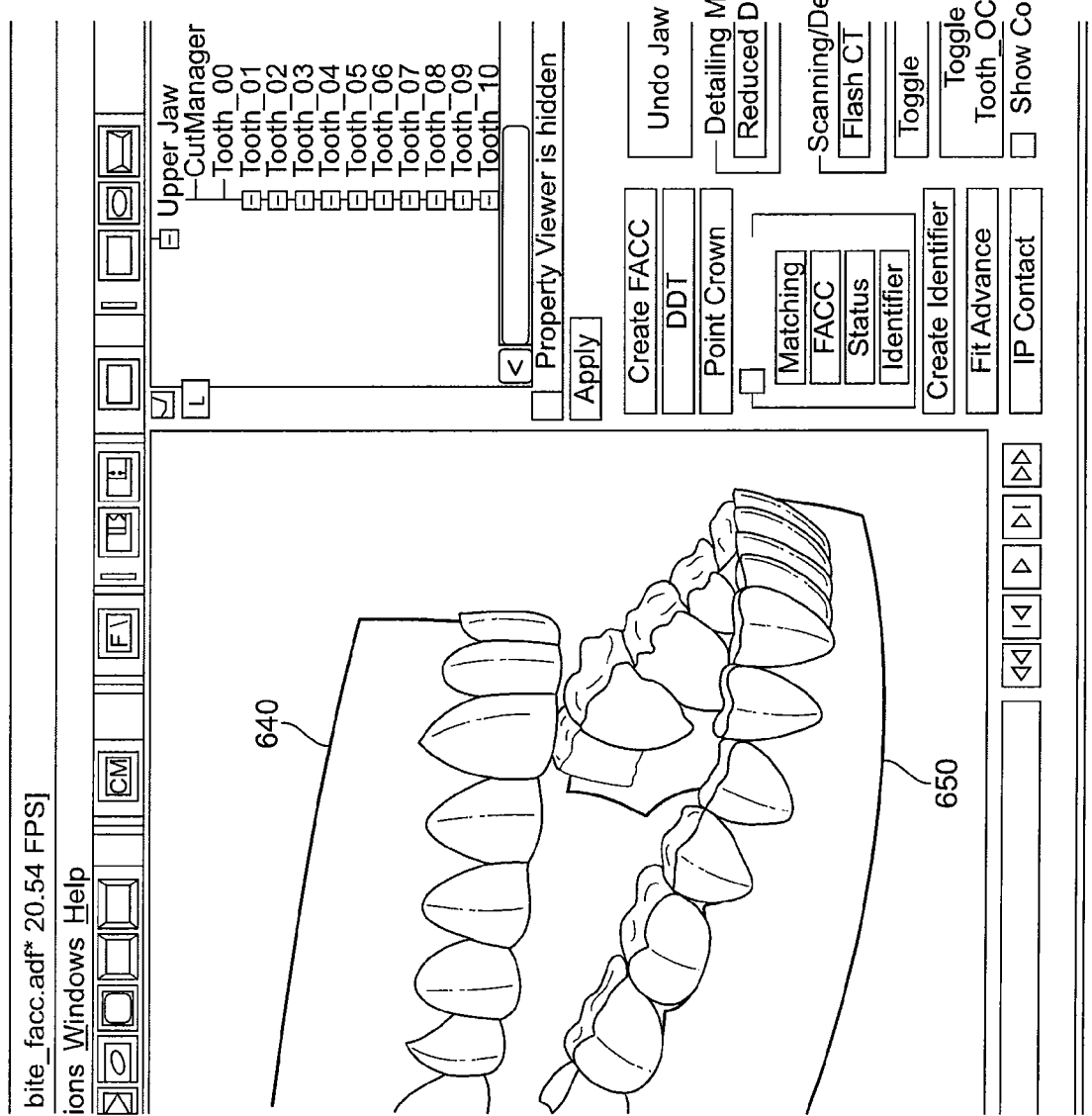
FIG. 7 is a screen shot showing a graphical representation of a three-dimensional model of a patient's upper and lower jaws based on a current digital data set representing teeth in their current positions, according to an embodiment of the present invention.

FIG. 7 is a screen shot showing a graphical representation of a three-dimensional model of a patient's upper and lower jaws 640, 650 generated from a Current Teeth Image. As described above, using a digital detailing tool (DDT), a technician pre-processes the Current Teeth Image by assigning and placing FACC's or unique current identifiers 74 on each tooth in the model. Unique current identifiers are landmarks on the teeth for the purposes of matching. Each FACC has a number associated with it and that is the tooth number, so the same tooth from the Previously Segmented Teeth Models and the Current Teeth Image should be in a similar location.

Figure 8:
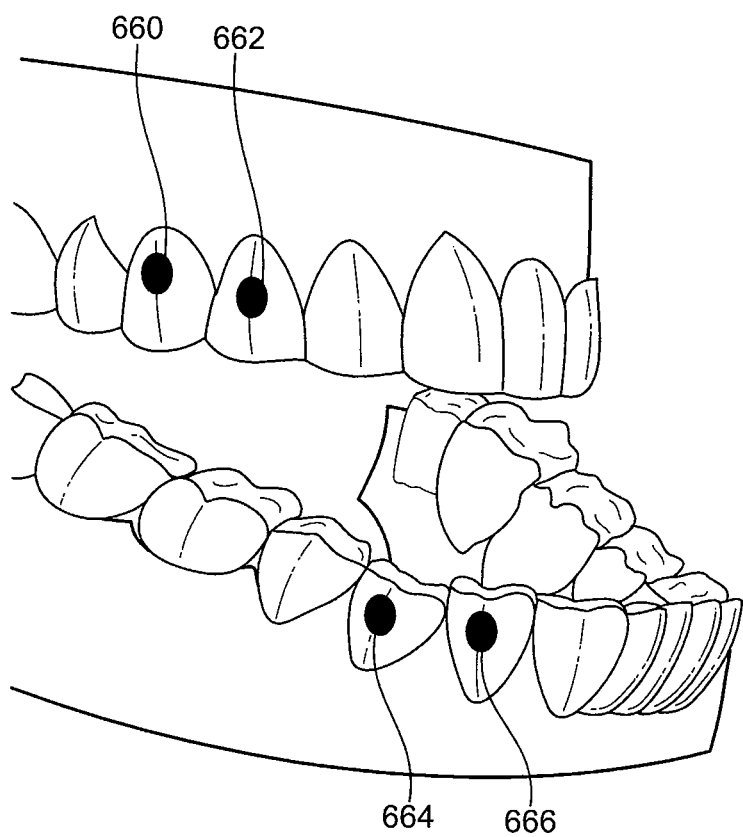
FIG. 8 is a graphical representation of a three-dimensional model of an initial match that can occur when the three dimensional model of digital translated images are overlaid on three dimensional model of the Current Teeth Image, according to one embodiment of the present invention.

FIG. 8 is a graphical representation of a three-dimensional model of a starting match that can occur when a Previously Segmented Teeth Model is overlaid on the Current Teeth Image, according to one embodiment of the present disclosure. The initial match provides a starting position for subsequent surface matching so that a good match is achieved.

If the initial matching algorithm determines that one or more teeth are mismatched, the initial matching algorithm cannot complete the initial matching satisfactorily because of teeth numbering irregularities or missing FACCs. In this instance, the initial matching algorithm will generate an informational dialog giving details of the mismatches allowing the technician to correct them and execute the initial matching algorithm again. Also shown in FIG. 8 are four attachments 660, 662, 664, 666 that have been optionally added to four of the patient's teeth.

See also, e.g., U.S. Pat. No. 8,075,306, entitled "System and Method for Detecting Deviations During the Course of an Orthodontic Treatment to Gradually Reposition Teeth," issued Dec. 13, 2011, the full disclosure of which is incorporated herein by reference, for further discussion of comparing an unsegmented representation of an actual arrangement of a patients teeth after treatment has begun, to a previously segmented model of the patient's teeth.

While the timing of the progress tracking steps described herein can be selected by the practitioner, typically at least general timing for conducting progress tracking measures of the present invention will be incorporated into the treatment plan and, therefore, will be pre-planned or planned at about the beginning of treatment or early on in the course of the patient's treatment (e.g., prior to the patient wearing a given set of appliances so as to reposition the teeth). Thus, in one embodiment of the invention, a treatment plan will include a prescribed timing for the planned tracking steps. The prescribed timing can include a specifically recommended date or may include a general increment of time (e.g., at treatment week 9, 10, 11, etc.), or can be based on the timing of other events of the treatment plan (e.g., after a patient wears a set of appliances).

Timing of progress tracking steps can be selected to occur based on a somewhat standardized treatment protocol or can be more particularly customized to an individual patient. More standardized protocols can take into account certain population statistics, generalized clinical expectations, and/or physiological parameters that can be used to generally predict rate of movement of a patient's teeth and the minimum length of treatment time necessary for the patient's teeth to progress off track if such progression is occurring. Clinical parameters can include, for example, root structure, including length, shape, and positioning, as well as certain jaw characteristics such as jaw bone density, patient age, gender, ethnicity, medications/health history profile, dental history including prior treatment with orthodontics, type of orthodontic treatment plan (extraction vs. non-extraction), and the like. Assuming a 2-week wear interval for each appliance, with a maximum tooth velocity of 0.25 mm/tooth per aligner, typically about 16 to 20 weeks of repositioning treatment (8 to 10 appliances) is required before movement of the teeth is substantial enough to detect a noncompliant or off track movement of the teeth, if such off track movement is occurring, though more drastic movements can produce off track movement after only a few weeks.

As set forth above, timing of tracking measures can be selected based on the particular movement(s) prescribed and/or characteristics of the patient being treated and, therefore, are said to be customized to the particular patient. For example, certain desired tooth movements in a treatment plan may be deemed either more unpredictable or at increased risk of moving off track and may require specifically timed tracking or monitoring. For example, for certain movements including, e.g., extrusions or rotations of round teeth (e.g., canines), more specific or frequent tracking may be desired. Additionally, certain physiological or clinical characteristics of the patient may be identified as indicating that particularly timed and/or frequency of tracking might be desired. Whether tracking is selected based on standardized protocols or more customized to the individual patient, tracking may or may not be selected to uniformly timed during the course of treatment. For example, a lower frequency of tracking measures may be desired or needed during certain portions or phases of treatment than others (e.g., space closure). Regardless of whether tracking timing is customized or more standardized, the selected timing will typically provide the additional advantage of efficiently planning tracking in the treatment plan to minimize unnecessary use of practitioner time and other resources.

Figure 9A:
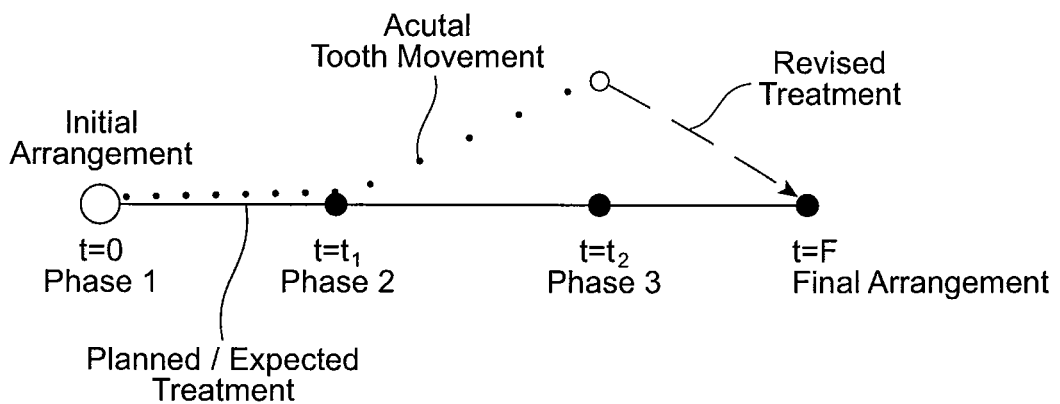
FIG. 9A through FIG. 9C show plurality of stages of teeth correction and revision of treatment, according to several embodiments of the present invention.
Figure 9B:
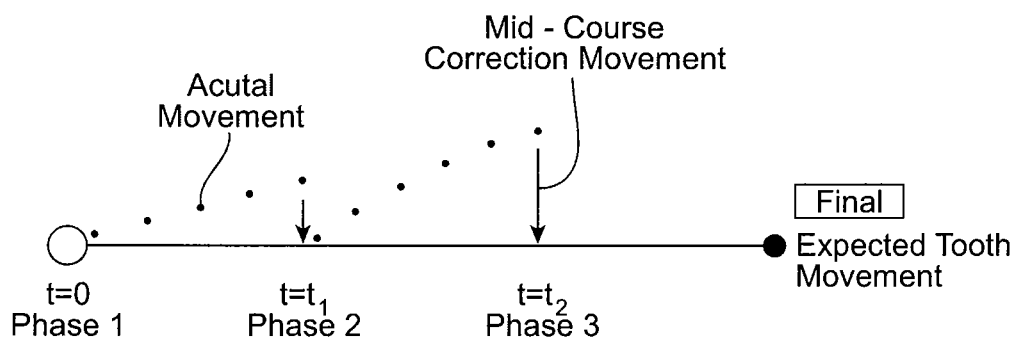
Figure 9C:
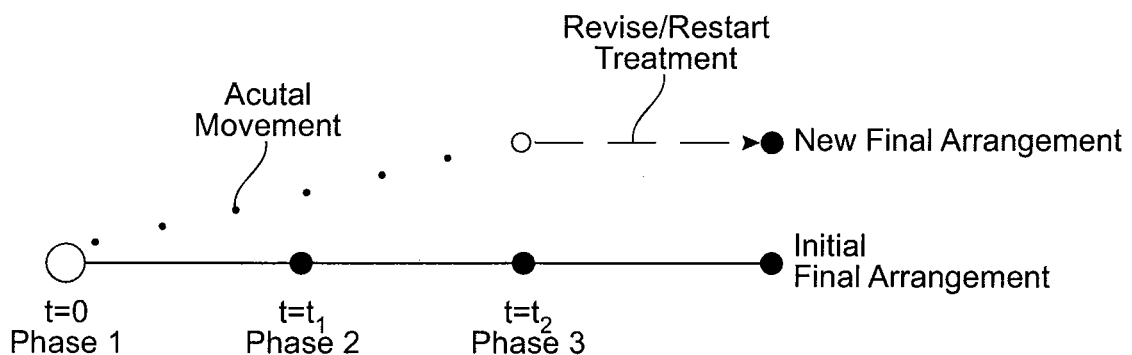

Once a determination is made that the patient's actual arrangement of teeth deviates from a planned arrangement and that the patient's teeth are not progressing as expected/planned, a change or correction in the course of treatment can be selected, for example, by generating a revised or modified treatment plan. Referring to FIGS. 9A-9C, revised treatment following determination that a patient's teeth are not progressing on track is described. As set forth above, a treatment plan includes a plurality of planned successive tooth arrangements for moving teeth along a treatment path from an initial arrangement to a selected final arrangement. The treatment plan, administration of sets of appliances to a patient according to the planned arrangements, can include a plurality of phases (1 through 4) where at time=0, the initial treatment plan begins. The initial treatment plan is illustrated by a solid line. Bite matching for a determination of whether a case is progressing "on track" or "off track", as described above (e.g., FIGS. 5, 6), can take place at one or more of the phases or points along the administration of treatment.

In particular, current tooth positions of the patient can be obtained from the patient any one or more phases and compared to segmented models of the patient's teeth according to an earlier or original treatment plan. Where teeth are determined to be deviating from the planned treatment plan or progressing "off track", as illustrated by broken lines, modification or revision of treatment plan can occur. In one embodiment, a revised treatment plan can include restaging the patient's treatment from the determined actual position to the originally determined final position (FIG. 9A). Revised treatment path (illustrated by dashed lines) can proceed directly toward the initially determined final position and need not attempt to redirect treatment back onto the original treatment path. In this case, while partial overlap/intersection of the revised treatment path with the original treatment path may occur, the revised treatment path will at least partially diverge from the initial treatment path and proceed directly toward the initially determined final arrangement of the teeth. Such an approach may be selected, for example, where retaining the initially determined final position is desired. This approach also advantageously permits use of the originally processed and segmented data, thereby allowing avoidance of costly processing steps.

Alternatively, a revised treatment plan can include a more direct "mid-course correction", in which the revised treatment plan includes a more direct path back toward the a planned arrangement of the initial treatment plan, as illustrated in FIG. 9B. While this approach may make use of the originally planned final arrangement, the more primary concern in this example type of correction is redirecting treatment back to the original treatment path, rather than from the actual position and more directly toward the original final position. In yet another embodiment, as illustrated in FIG. 9C, a revised treatment plan can include essentially "restarting" treatment, and generating a new final arrangement of the teeth, for example, from segmenting and staging a new impression of the teeth, and directing the patient's teeth from the actual arrangement to the newly determined final arrangement of the teeth.

Figure 10:
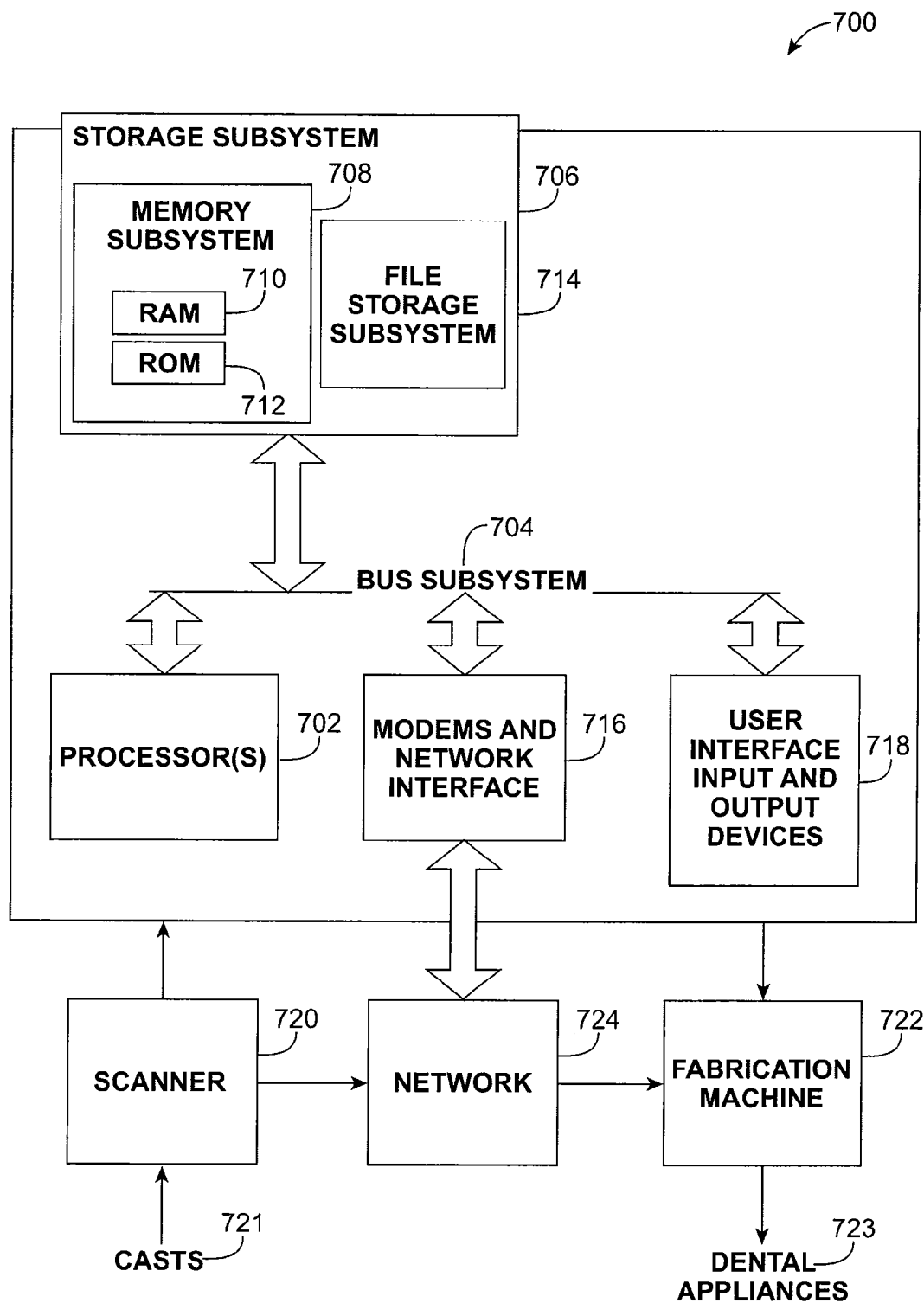
FIG. 10 is a block diagram illustrating a system for generating appliances in accordance with methods and processes of the present invention.

FIG. 10 is a simplified block diagram of a data processing system 700 that may be used in executing methods and processes described herein. The data processing system 700 typically includes at least one processor 702 that communicates with a number of peripheral devices via bus subsystem 704. These peripheral devices typically include a storage subsystem 706 (memory subsystem 708 and file storage subsystem 714), a set of user interface input and output devices 718, and an interface to outside networks 716, including the public switched telephone network. This interface is shown schematically as "Modems and Network Interface" block 716, and is coupled to corresponding interface devices in other data processing systems via communication network interface 724. Data processing system 700 can include, for example, one or more computers, such as a personal computer, workstation, mainframe, and the like.

The user interface input devices 718 are not limited to any particular device, and can typically include, for example, a keyboard, pointing device, mouse, scanner, interactive displays, etc. Similarly, various user interface output devices can be employed in a system of the invention, and can include, for example, one or more of a printer, display (e.g., visual, non-visual) system/subsystem, controller, projection device, audio output, and the like.

Storage subsystem 706 maintains the basic required programming, including computer readable media having instructions (e.g., operating instructions, etc.), and data constructs. The program modules discussed herein are typically stored in storage subsystem 706. Storage subsystem 706 typically comprises memory subsystem 708 and file storage subsystem 714. Memory subsystem 708 typically includes a number of memories (e.g., RAM 710, ROM 712, etc.) including computer readable memory for storage of fixed instructions, instructions and data during program execution, basic input/output system, etc. File storage subsystem 714 provides persistent (non-volatile) storage for program and data files, and can include one or more removable or fixed drives or media, hard disk, floppy disk, CD-ROM, DVD, optical drives, and the like. One or more of the storage systems, drives, etc may be located at a remote location, such coupled via a server on a network or via the Internet's World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 720 includes any means for obtaining an image of a patient's teeth (e.g., from casts 721), some of which have been described herein above, which can be obtained either from the patient or from treating professional, such as an orthodontist, and includes means of providing the image data/information to data processing system 700 for further processing. In some embodiments, scanner 720 may be located at a location remote with respect to other components of the system and can communicate image data and/or information to data processing system 700, for example, via a network interface 724. Fabrication system 722 fabricates dental appliances 723 based on a treatment plan, including data set information received from data processing system 700. Fabrication machine 722 can, for example, be located at a remote location and receive data set information from data processing system 700 via network interface 724.

It is understood that the examples and embodiments described herein are for illustrative purposes and that various modifications or changes in light thereof will be suggested to persons skilled in the art and are to be included within the spirit and purview of this application and the scope of the appended claims. Numerous different combinations are possible, and such combinations are considered to be part of the present invention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A computer-implemented method for managing a patient's progression through an orthodontic treatment plan, comprising:
    detecting, using a computer, a deviation of an actual arrangement of a patient's teeth from a planned arrangement of the orthodontic treatment plan, wherein the deviation is detected by comparing a previously segmented digital three-dimensional (3D) model of the planned arrangement to an unsegmented 3D digital representation of the actual arrangement; and
    generating, using a computer, instructions for fabricating at least one orthodontic appliance configured to correct the deviation.

2. The method of claim 1, further comprising receiving, on a computer, the unsegmented 3D digital representation of the actual arrangement of the patient's teeth after the orthodontic treatment plan has begun for the patient.

3. The method of claim 1, wherein the comparing comprises matching a surface of a tooth from the previously segmented digital 3D model to a tooth from the unsegmented 3D digital representation.

4. The method of claim 1, further comprising determining, based on the comparing, one or more positional differences between one or more teeth of the actual arrangement and one or more corresponding teeth of the planned arrangement.

5. The method of claim 4, wherein one or more positional parameters examined include at least one of tooth rotation, extrusion, intrusion, angulation, inclination, or translation.

6. The method of claim 1, further comprising generating a revised treatment plan configured to correct the deviation.

7. The method of claim 6, wherein the orthodontic treatment plan comprises a first plurality of planned successive arrangements for moving teeth along an initial treatment path from an initial arrangement toward a selected final arrangement and the revised treatment plan comprises a second plurality of successive arrangements to move the patient's teeth along a revised treatment path from the actual arrangement directly toward the selected final arrangement.

8. The method of claim 7, wherein the revised treatment path at least partially diverges from the initial treatment path.

9. The method of claim 1, further comprising adjusting a position of a tooth in the previously segmented digital 3D model if an error is generated after the comparing and the error is beyond a programmable threshold parameter value.

10. A computer system for managing a patient's progression through an orthodontic treatment plan, comprising:
one or more processors; and
memory, including instructions executable by the one or more processors to cause the computer system to at least:
detect a deviation of an actual arrangement of a patient's teeth from a planned arrangement of the orthodontic treatment plan, wherein the deviation is detected by comparing a previously segmented digital three-dimensional (3D) model of the planned arrangement to an unsegmented 3D digital representation of the actual arrangement, and
generate instructions for fabricating at least one orthodontic appliance configured to correct the deviation.

11. The computer system of claim 10, wherein the executable instructions further cause the computer system to:
pre-process the unsegmented 3D digital representation by assigning a facial axis of the clinical crown (FACC) identifier to each of one or more teeth in the unsegmented 3D digital representation; and
match one or more FACC identifiers of the unsegmented 3D digital representation with FACC identifiers of the previously segmented digital 3D model.

12. The computer system of claim 10, wherein the executable instructions further cause the computer system to generate a revised treatment plan in order to correct the deviation.

13. The computer system of claim 12, wherein the orthodontic treatment plan comprises a first plurality of planned successive arrangements for moving teeth along a treatment path from an initial arrangement toward a selected final arrangement and the revised treatment plan comprises a second plurality of successive arrangements to move the teeth along a revised treatment path from the actual arrangement directly toward the selected final arrangement.

14. The computer system of claim 10, wherein the orthodontic treatment plan includes a prescribed timing for tracking the patient's progress that is customized for the patient.

15. The computer system of claim 10, wherein the executable instructions further cause the computer system to determine one or more positional differences between one or more teeth of the actual arrangement and one or more corresponding teeth of the planned arrangement based on the comparing.

16. The computer system of claim 10, wherein the comparing comprises matching a surface of a tooth from the previously segmented digital 3D model to a tooth from the unsegmented 3D digital representation.

17. One or more non-transitory computer-readable storage media having stored thereon executable instructions that, when executed by one or more processors of a computer system for tracking a patient's progress through an orthodontic treatment plan, cause the computer system to at least:
detect a deviation of an actual arrangement of a patient's teeth from a planned arrangement of the orthodontic treatment plan, wherein the deviation is detected by comparing a previously segmented digital three-dimensional (3D) model of the planned arrangement to an unsegmented 3D digital representation of the actual arrangement; and
generate instructions for fabricating at least one orthodontic appliance configured to correct the deviation.

18. The one or more non-transitory computer-readable storage media of claim 17, wherein the orthodontic treatment plan comprises a first plurality of planned successive arrangements for moving teeth along a treatment path from an initial arrangement toward a selected final arrangement.

19. The one or more non-transitory computer-readable storage media of claim 18, wherein the previously segmented digital 3D model of the planned arrangement is generated based on the initial arrangement, the selected final arrangement, or an intermediate arrangement between the initial arrangement and the selected final arrangement.

20. The one or more non-transitory computer-readable storage media of claim 18, wherein the executable instructions further cause the computer system to generate a revised treatment plan in order to correct the deviation.

21. The one or more non-transitory computer-readable storage media of claim 20, wherein one or more teeth of the previously segmented teeth model are moved to the actual arrangement and the revised treatment plan utilizes the one or more teeth in both the actual arrangement and the selected final arrangement.

22. The one or more non-transitory computer-readable storage media of claim 20, wherein the revised treatment plan comprises a second plurality of successive arrangements to move the patient's teeth along a revised treatment path from the actual arrangement directly toward the selected final arrangement.

23. The one or more non-transitory computer-readable storage media of claim 17, wherein the comparing comprises matching a surface of a tooth from the previously segmented digital 3D model to a tooth from the unsegmented 3D digital representation.

* * * * *